United States Patent
Rizzi

(10) Patent No.: US 9,938,247 B2
(45) Date of Patent: Apr. 10, 2018

(54) COMBINED REACTOR FOR HIGH-PRESSURE SYNTHESIS OF MELAMINE

(71) Applicant: Casale SA, Lugano (CH)

(72) Inventor: Enrico Rizzi, Casnate con Bernate (IT)

(73) Assignee: Casale SA, Lugano (CH)

( * ) Notice: Subject to any disclaimer, the term of this patent is extended or adjusted under 35 U.S.C. 154(b) by 0 days.

(21) Appl. No.: 15/118,394

(22) PCT Filed: Jan. 30, 2015

(86) PCT No.: PCT/EP2015/051950
§ 371 (c)(1),
(2) Date: Aug. 11, 2016

(87) PCT Pub. No.: WO2015/124409
PCT Pub. Date: Aug. 27, 2015

(65) Prior Publication Data
US 2017/0166536 A1    Jun. 15, 2017

(30) Foreign Application Priority Data
Feb. 18, 2014  (EP) .................................... 14155561

(51) Int. Cl.
| C07D 251/62 | (2006.01) |
| C07D 251/60 | (2006.01) |
| B01J 19/24 | (2006.01) |
| B01J 4/02 | (2006.01) |
| B01J 3/04 | (2006.01) |
| B01J 10/00 | (2006.01) |

(52) U.S. Cl.
CPC .............. *C07D 251/60* (2013.01); *B01J 3/04* (2013.01); *B01J 4/02* (2013.01); *B01J 10/00* (2013.01); *B01J 19/246* (2013.01); *C07D 251/62* (2013.01); *B01J 2219/24* (2013.01)

(58) Field of Classification Search
CPC .. C07D 251/60; C07D 251/61; C07D 251/62; B01J 10/00; B01J 18/24; B01J 3/04; B01J 4/02

USPC .................................................. 544/201, 203
See application file for complete search history.

(56) References Cited

U.S. PATENT DOCUMENTS

| 1,988,766 | A |  | 1/1935 | Aldridge |  |
| 3,271,116 | A |  | 9/1966 | Hazelton |  |
| 3,432,274 | A |  | 3/1969 | Abe et al. |  |
| 5,486,339 | A |  | 1/1996 | Bizzotto |  |
| 6,815,545 | B2 | * | 11/2004 | Bucka .................. | C07D 251/60 544/201 |
| 7,041,822 | B2 |  | 5/2006 | Coufal |  |
| 7,311,759 | B2 |  | 12/2007 | Schroder et al. |  |
| 2004/0054175 | A1 |  | 3/2004 | Bucka et al. |  |
| 2007/0232801 | A1 |  | 10/2007 | Bairamijamaf |  |

FOREIGN PATENT DOCUMENTS

| FR | 1416096 A | 10/1965 |
| WO | 01/98281 A1 | 12/2001 |
| WO | 03/045538 A1 | 6/2003 |
| WO | 2011/161215 A1 | 12/2011 |

OTHER PUBLICATIONS

International Search Report issued in connection with PCT/EP2015/051950.
International Preliminary Report on Patentability issued in connection with PCT/EP2015/051950.
European Search Report issued in connection with EP 14155561.

* cited by examiner

*Primary Examiner* — Venkataraman Balasubramanian
(74) *Attorney, Agent, or Firm* — Akerman LLP

(57) ABSTRACT

A reactor and associated process for the high-pressure synthesis of melamine from urea, comprising a primary step of conversion of the urea into crude melamine inside a first chamber delimited by a shell inside a reactor body and a secondary step of stripping said crude melamine melt inside a second reaction chamber, which is coaxial with and situated outside said first chamber, inside the same reactor body.

20 Claims, 4 Drawing Sheets

COMBINED REACTOR FOR HIGH-PRESSURE SYNTHESIS OF MELAMINE

This application is a national phase of PCT/EP2015/051950, filed Jan. 30, 2015, and claims priority to EP 14155561.5, filed Feb. 18, 2014, the entire contents of both of which are hereby incorporated by reference.

FIELD OF THE INVENTION

The invention relates to the synthesis of melamine from urea. The invention relates in particular to a reactor and a related process for the high-pressure synthesis of melamine.

PRIOR ART

The processes for the synthesis of melamine from urea are commonly classified as low-pressure catalytic processes, typically below 1 MPa, and high-pressure non-catalytic processes, typically above 7 MPa. These processes are well-known in literature (see for example Ullmann's Encyclopedia of Industrial Chemistry, 6th ed., vol. 21, p. 205).

One of the known high-pressure synthesis processes, as described for example in U.S. Pat. No. 6,815,545, comprises essentially three steps: an endothermic reaction which converts urea into melamine inside a first reactor, called primary reactor; a second step for removal of the carbon dioxide ($CO_2$) by introducing gaseous ammonia, and reduction of the content of by-products which are converted into melamine with an increase in conversion, inside a second reactor called secondary reactor or stripping reactor; a third step during which the gases separated in the top part of the primary and secondary reactors (called "off-gases") are conveyed away for washing or scrubbing with urea before being conveyed to the urea plant.

A plant lay-out which operates using this process is typically the following:

The plant comprises a primary reactor, a secondary reactor and a scrubber, which are formed as separate cylindrical bodies. The liquid urea or urea melt is supplied to the primary reactor where the first reaction stage takes place, which is the endothermic conversion into melamine; the effluent of said reactor is directed to the second reactor, where it undergoes a process of stripping of the gases contained therein, by means of gaseous ammonia. The liquid melamine is generally kept inside this secondary reactor for a certain dwell time (ageing of melamine) so as to allow the by-products formed inside the primary reactor to be converted into melamine. The liquid effluent from the secondary reactor (melamine melt) may be conveyed away for a subsequent further purification step.

The gases released inside the primary reactor and inside the secondary reactor form a stream of so-called off-gases containing mainly ammonia and $CO_2$ with small amounts of melamine; said stream of off-gases undergoes washing with urea melt, inside the scrubber. The urea melt is thus heated before being supplied to the primary reactor; the off-gases at the scrubber outlet, which are melamine-free, are conveyed away and for example recycled for urea synthesis.

The pressure is generally between 70 and 250 bar (7-25 MPa), typically about 100-120 bar (10-12 MPa).

A known primary reactor configuration is described in U.S. Pat. No. 6,815,545. The reactor comprises a vertical cylindrical body; a coaxial duct inside the shell which is open at the top; a series of heating bodies arranged around said duct so as to provide heat to the endothermic reaction. Said heating bodies are for example vertical bayonet tubes fed with liquefied salts. The urea is fed to the bottom of the central duct so that the reaction of conversion starts inside said duct and is completed in the annular section of the reactor; the crude melamine fills nearly entirely the reactor, while the off-gases are separated at the top. A header for collecting the melamine is normally situated in the top part of the reactor, above the duct.

An example of secondary reactor is described in U.S. Pat. No. 7,041,822. It is essentially a cylindrical vertical reactor provided with suitable inlets for the crude melamine supplied from the primary reactor and for the stream of gaseous ammonia (stripping agent), and outlets for the treated (stripped) melamine and for the off-gases. U.S. Pat. No. 7,311,759 describes an example of a scrubber, also formed substantially as a vertical and axially symmetrical cylindrical body, with counter-flow of the off-gases and urea.

The apparatuses described, i.e. primary reactor, secondary reactor and scrubber, are costly owing to the strict operating conditions which require high-quality materials (e.g. nickel alloys) and the fairly complex constructional designs. The presence of three separate cylindrical bodies, among other factors, increases the cost of the plant. Each cylindrical body requires its respective foundations and also the cost of the connecting pipes (again made of high-quality material) is high. Another disadvantage of the configuration comprising separate reactors is that the off-gases are partly released inside the primary reactor and partly inside the secondary reactor, thus requiring two ducts which have to be connected upstream of the scrubber inlet, thus resulting in a more complex piping.

In order to reduce this cost, WO 2011/161215 discloses a combined reactor which combines the functions of primary reactor, secondary reactor and scrubber in a single pressurised body. Said combined reactor is formed essentially by a horizontal cylindrical body which incorporates the primary and secondary reactor sections and by a vertical tower dome which operates as a scrubber.

This combined reactor offers the advantage of combining three pressured apparatuses in a single apparatus. It has, however, a number of drawbacks and disadvantages.

A first disadvantage consists in the fact that said combined reactor no longer has the axial symmetry of the conventional apparatuses, in particular in the primary and secondary reactor sections. This results in the need for careful redesign of the synthesis process which is strictly dependent on the fluid dynamics and therefore the actual form of the said apparatuses. The melamine synthesis process is, as is well-known, very complex and the conversion to a completely different geometrical form increases the design and optimization costs associated with the fluid dynamics and process aspects.

Furthermore, the horizontal body may have a large "footprint" on the ground. Vertical apparatuses are generally preferred because the foundations are simpler and they make better use of the available area for the plant. This fact is of great importance in the case of revamping of an existing plant where the new or modified apparatuses must be arranged in the available space or in the space occupied by the pre-existing apparatuses. Generally speaking there is little space available in the plant and therefore the solution of a horizontal reactor may not be practical.

Another drawback consists in the fact that the dome must have a large diameter, comparable to the diameter of the horizontal body, in order to ensure a slow speed of the gases. Consequently, the connection between the horizontal body and the dome is costly to achieve, especially in view of the high operating pressure. A large-size opening must be made in the horizontal body, and said opening requires suitable reinforcement. All this increases the manufacturing costs and therefore partly offsets the savings achieved by replacing three apparatuses with a single apparatus.

The flow of the off-gases is not entirely satisfactory because the gases output from the secondary reactor are collected at the top of the horizontal vessel and are then transferred horizontally until they reach the dome inlet, with a consequent non-uniform distribution of the said gases inside the scrubber section.

U.S. Pat. No. 3,432,274 and U.S. Pat. No. 5,489,339 disclose reactors for the synthesis of melamine at high pressures with reaction zones one above the other.

SUMMARY OF THE INVENTION

The invention aims to overcome these drawbacks by providing a combined melamine reactor able to cater for the primary reaction and secondary reaction and in some cases the scrubbing of the gases too, inside a single pressurised body, without however the drawbacks discussed further above.

The idea underlying the invention is to provide, inside a vertical reactor, a coaxial secondary reaction chamber outside and around a primary chamber. Moreover, the top of the reactor may be configured to operate as scrubber, resulting in the combination of the three main components in a single vertical reactor. In this way a vertically extending reactor and the axial symmetry, which have proved to be effective, are retained.

The objects are achieved with a reactor for the synthesis of melamine from urea, using the high-pressure non-catalytic process according to the accompanying claim 1, which comprises a vertical reactor body and further comprises:

a shell coaxial with said vertical body and situated inside said vertical body which delimits inside the reactor a first reaction chamber (5, 6) and a second reaction chamber which are coaxial with each other, said second reaction chamber being arranged coaxially around said first chamber;

at least one inlet for urea melt arranged to introduce urea melt into said first reaction chamber;

at least one path for supplying the effluent from said first chamber into said second chamber;

at least one inlet arranged to introduce gaseous ammonia into said second reaction chamber; and at least one header for collecting liquefied melamine from said second reaction chamber.

The first reaction chamber and the second reaction chamber are also termed inner reaction chamber and outer reaction chamber, respectively.

Preferably, the reactor comprises a central duct coaxial with and situated inside said shell, which delimits an internal zone and a peripheral zone of said first reaction chamber. In this case, more preferably, said at least one urea melt inlet is designed in order to introduce urea melt into said internal zone of the first reaction chamber.

More advantageously, said peripheral zone is internally delimited by the central duct and externally delimited by the shell.

Preferably said second chamber is substantially annular. Preferably, said shell is cylindrical and consequently said second (outer) chamber is substantially cylindrical and annular around the first (inner) chamber. More preferably, the reactor body, the central duct (where provided) and the second shell are cylindrical and coaxial with each other.

Said second chamber works as secondary stripping reactor, since it is supplied with gaseous ammonia. The first chamber and the second chamber may therefore be defined respectively as the primary conversion section and the secondary stripping section.

Said shell essentially divides the inside of the reactor into two communicating sections: a primary section inside the shell and a secondary or stripping section which is formed by said second reaction chamber.

The primary section comprises essentially two zones communicating with each other: a zone inside the central duct, where the reaction starts, and a zone between the duct and the shell, where the heating bodies are preferably installed and the reaction is completed and the crude melamine is collected at the top.

Since the two sections communicate with each other, the crude melamine synthesised in the first section (first reaction chamber) flows into the second section (second reaction chamber).

In a preferred embodiment, said internal shell extends up to a height greater than the height of the duct and an edge of said shell acts as an overflow distributor for supplying the second reaction chamber.

Preferably the reactor comprises heating bodies which are housed in said zone between the duct and the shell so as to supply heat to the mass of melamine melt and maintain a high temperature inside the reactor so as to fuel the endothermic reaction for conversion of urea to melamine.

The heating bodies may consist of tubes passed through by a fluid. In a preferred embodiment, said heating bodies comprise bayonet tubes passed through by a hot fluid, for example liquefied salts. In other embodiments they may comprise a conventional tube bundle or other equivalent means. The particular form of the heating bodies is not essential for the invention.

Preferably, the reactor comprises a gaseous ammonia distributor configured to introduce ammonia in a distributed manner at the base of said second chamber.

For example the ammonia distributor may be formed as a toroidal body positioned at the base of the second chamber.

The reactor advantageously also comprises a header suitable for collecting the liquefied melamine from the bottom of said second chamber, more preferably in a distributed manner.

The reactor thus designed offers the major advantage of combining the functions conventionally assigned respectively to the primary reactor (conversion of urea into melamine) and to the secondary reactor (stripping of $CO_2$ with ammonia), while maintaining the vertical design with axial symmetry. In this way the well-known fluid dynamics associated with an axially symmetrical process is maintained and even further improved.

An advantage of the invention is the elimination of a pressure apparatus (i.e. the secondary reactor), this being obtained against a small increase in the outer diameter of the new apparatus, while the overall height remains substantially the same as that of the single primary reactor. For example, the internal diameter of an apparatus which combines the two reactors, according to the present invention, is only about 20% greater than the diameter of a primary reactor according to the prior art. Moreover, the second shell is not exposed to a significant difference in pressure and, although made of high-quality material, may have a small thickness and therefore not have a high cost. It may therefore be stated that the combined reactor according to the invention has a cost slightly greater than the cost of a normal primary reactor, but offers the great advantage of removing the secondary reactor and the associated foundation as well as the piping (also made of high-quality material) for transferring melamine from the primary reactor to the secondary one. The off-gas collection piping is also simplified because the gases must be collected from a single reactor rather than from two reactors.

The invention has also important advantages from the point of view of the process. In one of the preferred embodiments, the melamine enters the second chamber overflowing from the top edge of the inner shell. This means that the transfer of the melamine from the primary reaction zone to the secondary reaction zone occurs uniformly and in an axially symmetrical manner. In conventional primary reactors, the melamine is drawn off from a single point, creating local disturbance inside the reactor. It can be understood, therefore, that, thanks to the invention, the operating conditions of primary conversion of urea into melamine are improved and in particular a greater uniformity of the conditions inside the reactor is achieved.

As regard this aspect, it should also be noted that the prior art plants with separated reactors have a melamine output from the primary reactor which is conveyed to an opening and then distributed again inside the secondary reactor. With the new configuration of the invention, melamine is already distributed uniformly and in a completely symmetrical manner in relation to the ammonia distributor located at the bottom of the chamber operating as a secondary reactor. This results in a greater efficiency from the point of view of the process.

Another advantage consists in the off-gases outlet which is common to the top part of the apparatus and is exactly symmetrical. The off gases emerging from both the first chamber and the second chamber are collected at the top of the reactor. There is therefore a single off-gas output stream from the apparatus.

In a preferred embodiment, the reactor also comprises a scrubber section situated in the top part of the said reactor, namely above the primary section and secondary section described above. Said scrubber section collects the gases which emerge from the underlying sections and is fed with urea melt, for example with part of the feed urea. Said urea melt, after counter-flow contact with the gases, is collected at the base of the scrubber section and conveyed to the first reaction chamber. Preferably, the reactor comprises a flat flue which delimits the bottom of the scrubber section, allows the gases to rise up and collects the urea melt.

The scrubber section may also be contained inside the same outer shell. The scrubber section, in some embodiments, may have a smaller diameter, with a conical transition part. However it may be preferred to maintain the diameter of the shell of the primary and secondary sections, with the advantage of obtaining low speed of the gases.

Feeding of the urea from the scrubber to the primary section is preferably performed outside the reactor.

The addition of the scrubber section has the advantage of combining three apparatuses in one, removing the costs for the scrubber, the respective foundations and the connection piping, while maintaining the vertical design and the axial symmetry of the combined reactor.

The axial symmetry of the flow of the off-gases from the primary and secondary sections towards the scrubber is a further advantage of the invention.

To summarise, in the various embodiments of the invention, including those which combine the primary reactor and secondary reactor, and those which also combine the scrubber, the following advantages are achieved: a relatively simple reactor design; a vertical configuration which saves space and generally allows existing foundations to be used in the case of replacement of an existing vertical reactor; a substantial axial symmetry of the process fluid dynamics, which is advantageous especially in a complex reaction such as melamine synthesis, where a local deviation from the desired process conditions may reduce the efficiency and/or form undesirable by-products. The invention also helps to ensure a stable reaction and limit the formation of by-products.

Another aspect of the invention relates to a melamine synthesis process according to the accompanying claims. Said process comprises a primary conversion step inside a reactor body, resulting in a crude urea melt, and a secondary step of stripping of said crude melamine melt inside a second reaction chamber, which is arranged coaxially around said first chamber, inside said reactor body.

The advantages will emerge even more clearly with the aid of the detailed description below relating to a number of preferred embodiments.

DETAILED DESCRIPTION OF PREFERRED EMBODIMENTS

Figure 1:
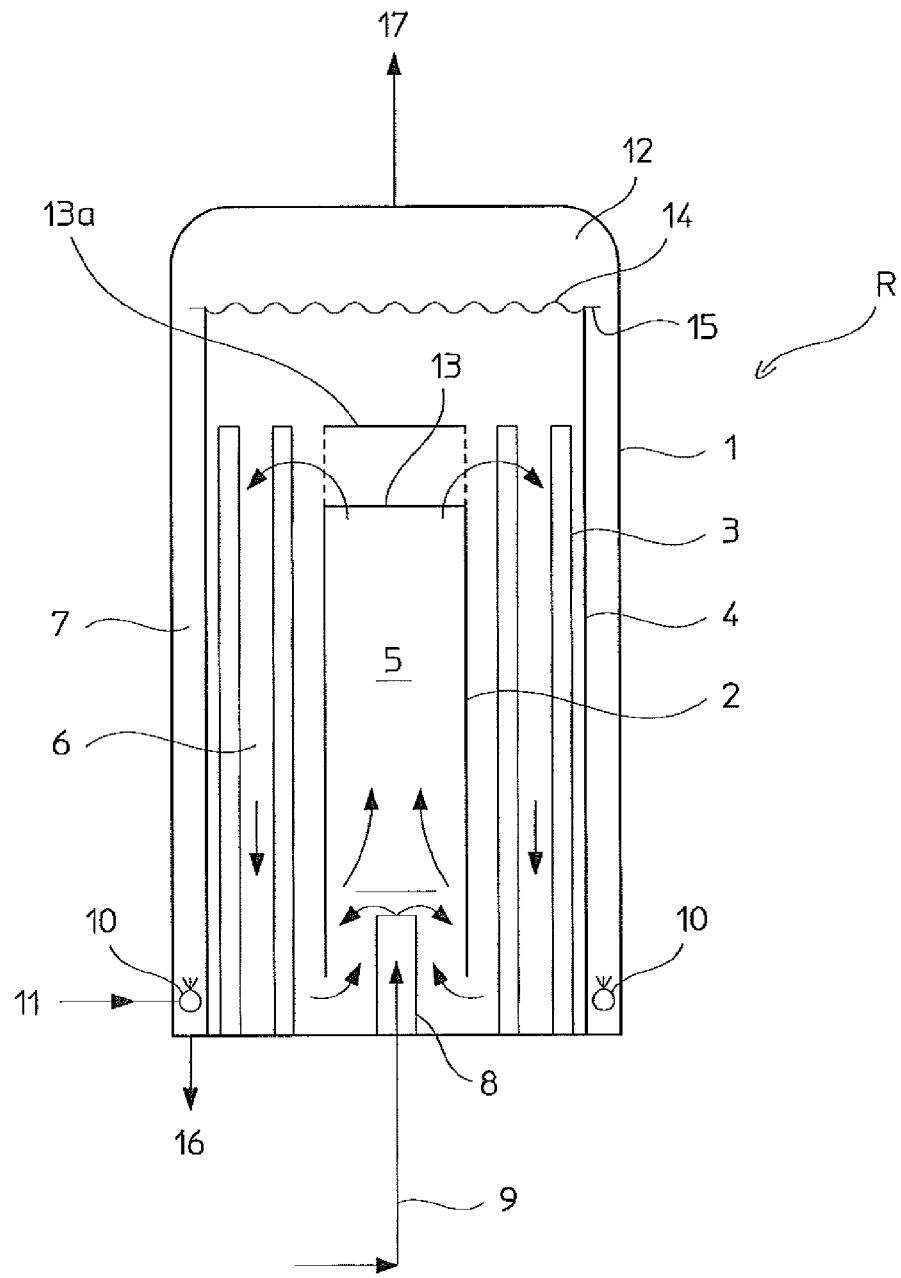
FIG. 1 is a cross-sectional diagram of a combined reactor in a first embodiment.

FIG. 1 shows a combined reactor R for the synthesis of melamine from urea, using the high-pressure non-catalytic process, which essentially comprises: a vertical body 1, a central duct 2, a plurality of heating pipes 3 outside the central duct 2, a shell 4 coaxial with and situated outside of the heating pipes 3.

Both the central duct 2 and the shell 4 are preferably cylindrical.

The shell 4 defines a first inner reaction chamber composed of an internal zone 5 delimited by the central duct 2 and a peripheral zone 6, outside the central duct 2, housing the heating pipes 3. A second outer reaction chamber 7, with a substantially annular shape, is delimited between said shell 4 and the wall of the reactor body 1.

Accordingly, the outer chamber 7 is arranged coaxially around the inner chamber 5.

The reactor R comprises at least one inlet 8 for urea melt 9, which is designed to introduce the urea melt into the internal zone 5 delimited by the central duct 5. The reactor further comprises a toroidal distributor 10 housed at the bottom of the annular chamber 7 and connected to a line 11 which supplies ammonia in the gaseous state.

Advantageously, as shown, the shell 4 extends inside the reactor up to a height which is greater than the height of the duct 2; preferably almost to the top of the reactor, leaving a top chamber 12 for the separation of the gases freed during the reaction.

The shell 4 may be defined as a low-pressure shell, since it is not subjected to a significant difference of pressure between the inside and outside. Therefore said shell 4 may be formed with a small thickness and therefore at a low cost and with a low weight.

The top section 13 of the duct 2 is open so that the liquid melamine may pass from the zone 5 to the zone 6 so that a circulation is formed inside the first reaction chamber. Advantageously an impingement deflector plate 13a is provided above the opening of the duct 2 in order to convey the liquid into the zone 6, as illustrated by the arrows in FIG. 1. In some embodiments, lateral openings may also be provided in the duct 2 so as they allow the melamine to flow into said zone 6.

In normal operating conditions, the liquid melamine fills the reactor R, reaching the level shown in the figure by the line 14, and flows over the top edge 15 of the shell 4, thus passing into the annular chamber 7. The edge 15 may be suitably shaped to favour overflowing of the liquid.

Inside said annular chamber 7 the liquid melamine undergoes stripping as a result of the stream of counter-flowing gaseous ammonia supplied uniformly by the toroidal distributor 10. The stripped melamine 16 thus obtained is discharged from the reactor at the bottom of the chamber 7; the gases released during the process and containing $CO_2$ and ammonia are collected inside the chamber 12 and discharged from the line 17. Said gases may be supplied to a conventional scrubber.

As seen in FIG. 1, the reactor R basically provides a primary conversion section, corresponding to the chambers 5 and 6 inside the shell 4, and a secondary stripping section, consisting of the annular chamber 7. Said chambers 5 and 6 and said chamber 7 communicate with each other via the top edge 15 of the shell 4.

Owing to the arrangement of the stripping section, which according to the invention is coaxial with and outside the primary conversion section, the two sections may be combined in a single body while maintaining the vertical configuration and the axial symmetry. It should be noted that both the flow of the liquid between the chambers 5 and 6 and then the chamber 7 and the supply of the stripping ammonia from the distributor 10 take place in a substantially axially symmetrical manner. Consequently, the fluid dynamic conditions inside the reactor are also substantially axially symmetrical, thus improving the conversion efficiency and the stability of the chemical reaction.

Figure 2:
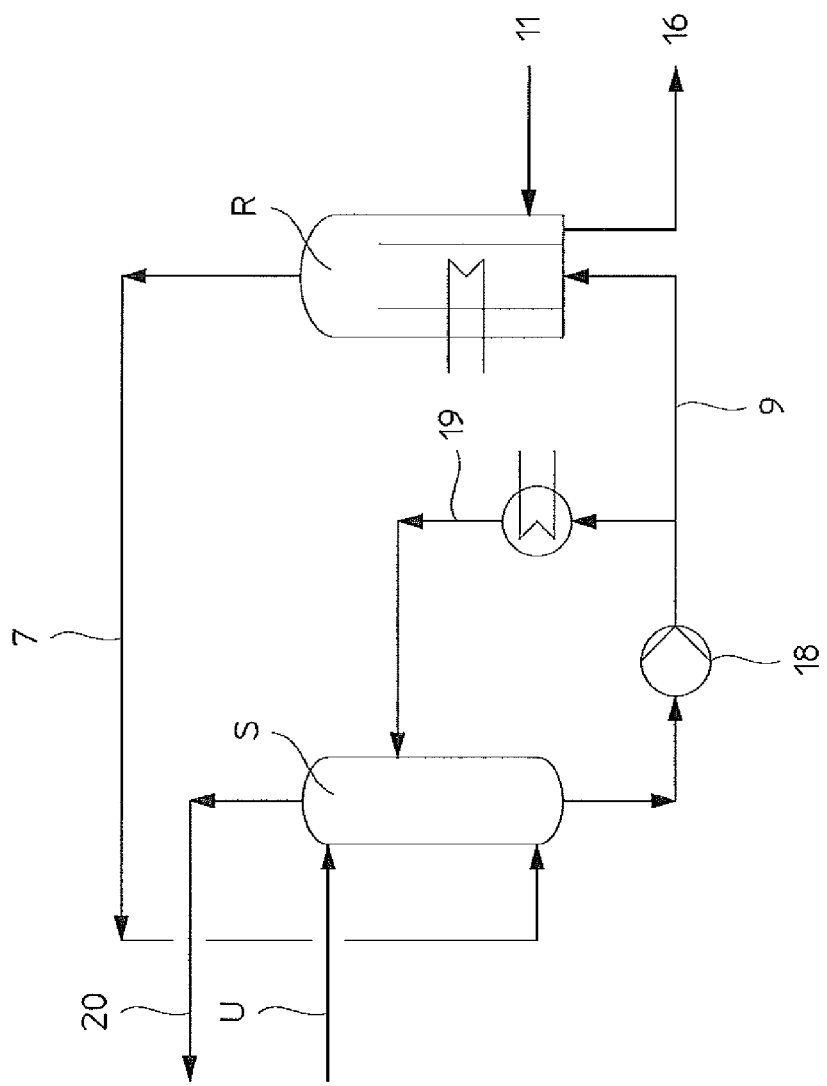
FIG. 2 is a simplified diagram of a plant comprising the combined reactor according to FIG. 1.

FIG. 2 shows an example of incorporation of the reactor R according to FIG. 1 in a melamine plant.

The stream of off-gases 17 flowing out of the reactor R is conveyed to the bottom of a separate scrubber S in which washing of the gases with the feed urea U, for example urea melt with a high purity (e.g. 99.5% or more), is performed. Said scrubber S may be a conventional scrubber.

The plant comprises a pump 18 for circulating the urea. Part of the urea leaving the scrubber S is recirculated inside the said scrubber via the line 19 and the remainder forms the feed stream 9 for the combined reactor R.

The stream of off-gases 20 leaving the scrubber is for example recycled in order to produce urea.

Figure 3:
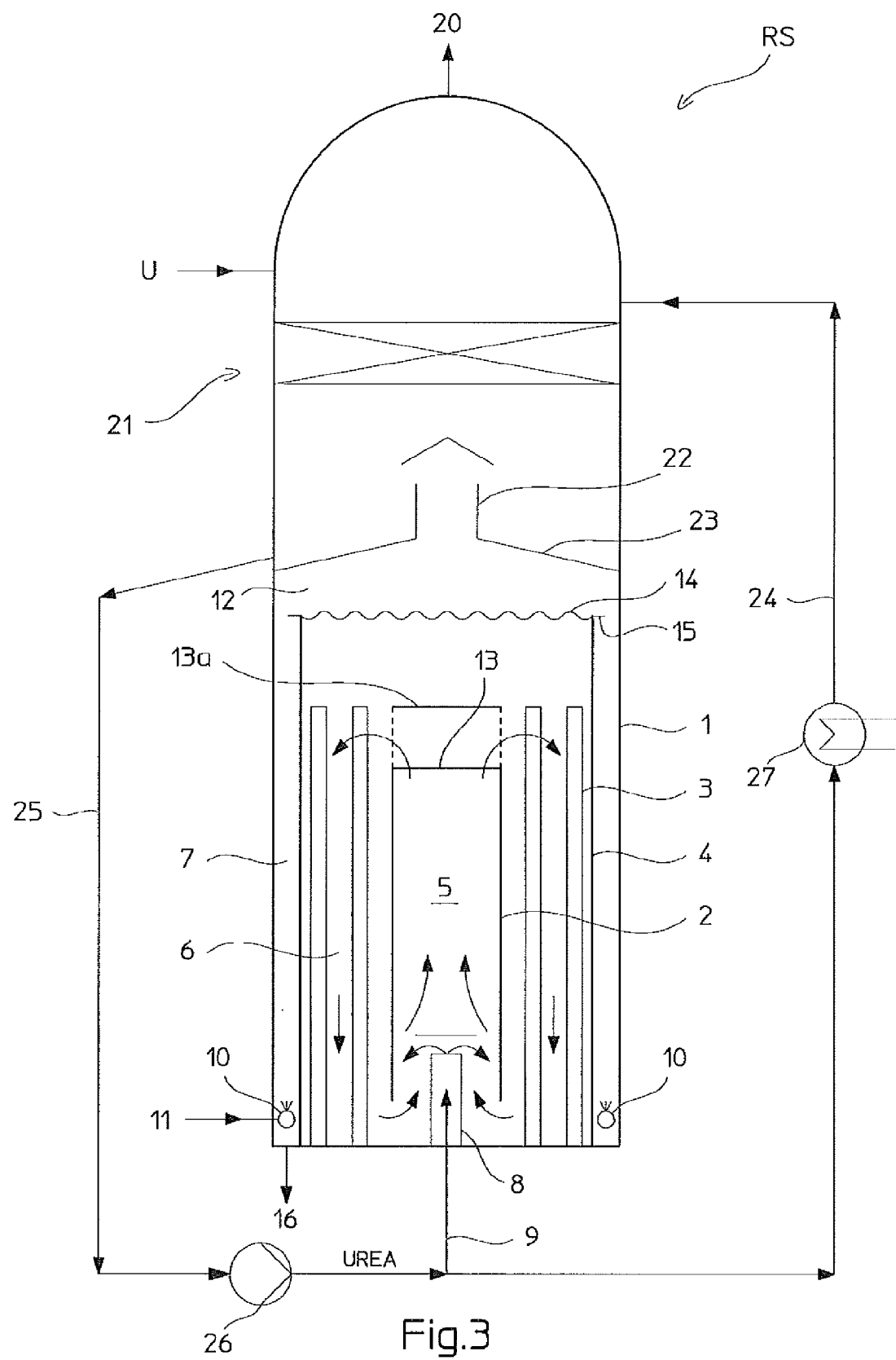
FIG. 3 is a cross-sectional diagram of a combined reactor in a second embodiment, also comprising a scrubber section.

FIG. 3 shows an example of a combined reactor, denoted as RS, which also includes a scrubber section.

The bottom part of the reactor RS is substantially formed as shown in FIG. 1; the top part comprises a section 21 which operates as a scrubber. Said section 21 communicates with the bottom part via a flue 22 provided with a plate 23 for collecting the liquid phase.

During operation, the gases coming from the chambers 5, 6 and 7 are conveyed to the scrubber section 21 via the flue 22; part of the liquid urea 24 is supplied to the top part of the scrubber, where it forms a counter-flow with the gases. The fresh urea U is also supplied to the top of the scrubber 21 in order to perform final washing of the off-gases. The liquid urea is collected on the plate 23 and returns to the reaction chamber 5 along a line 25, optionally via a pump 26. The diagram also shows an exchanger 27 for cooling the urea supplied to the scrubber section.

It can be noted that the flow of off-gases coming from the top of the reactor RS corresponds to the flow 20 in FIG. 2, being formed by gases already subjected to the scrubbing process inside the section 21.

Figure 4:
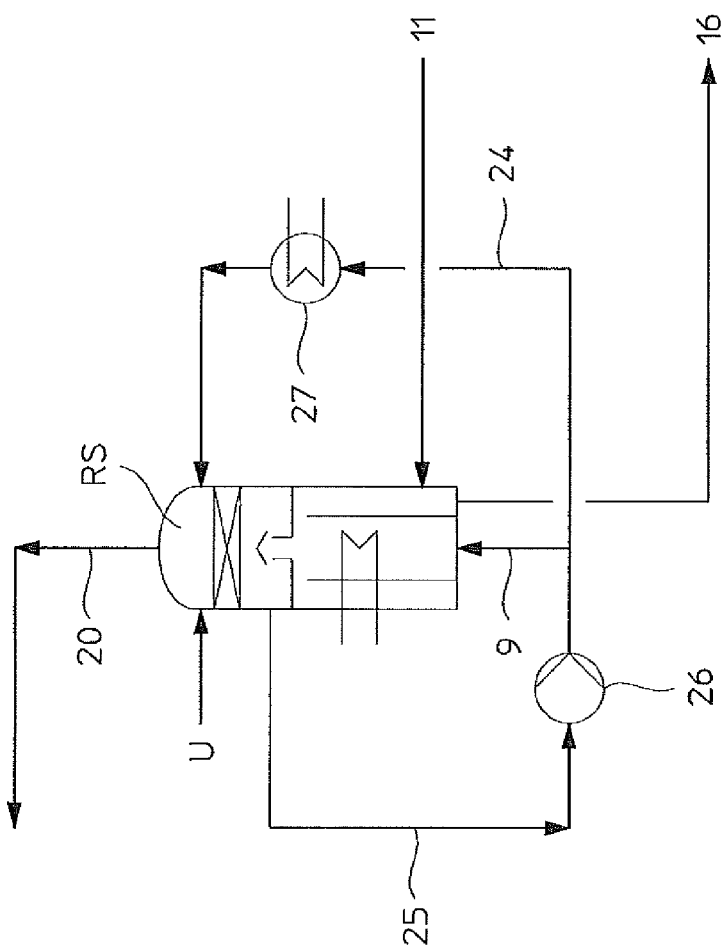
FIG. 4 is a simplified diagram of a plant comprising the combined reactor according to FIG. 3.

FIG. 4 shows a diagram of a plant comprising the combined scrubber/reactor RS according to FIG. 3.

The invention claimed is:

1. A reactor for the synthesis of melamine from urea, using the high-pressure non-catalytic process, comprising:
   a vertical reactor body having a urea melt inlet and a melamine outlet;
   an inner reaction chamber and an outer reaction chamber, said outer reaction chamber being arranged coaxially around said inner chamber;
   said at least one urea melt inlet arranged to introduce urea melt into said inner reaction chamber, wherein the urea melt contacts a circulating liquid mixture in the inner reaction chamber;
   at least one path arranged to feed a raw melamine product effluent from said inner chamber into said outer chamber;
   at least one ammonia inlet arranged to introduce gaseous ammonia into said outer reaction chamber, wherein said gaseous ammonia, in the outer chamber reaction chamber, has upward flow counter-current with a descending flow of said raw melamine product, so that the outer reaction chamber acts as a stripping chamber for said raw melamine product; and
   at least one melamine header for collecting liquid melamine from said outer reaction chamber, said melamine header being connected to said melamine outlet, so that the melamine output of the reactor is withdrawn from the outer reaction chamber.

2. The reactor according to claim 1, comprising a shell coaxial with said vertical body and situated inside said vertical body, wherein said shell delimits inside the reactor said inner reaction chamber and said outer reaction chamber.

3. The reactor according to claim 2, said outer reaction chamber being delimited between said shell and said body of the reactor.

4. The reactor according to claim 3, comprising a central duct coaxial with and situated inside said shell, which delimits an inner zone and a peripheral zone of said inner reaction chamber.

5. The reactor according to claim 4, said urea melt inlet being designed to introduce urea melt into said inner zone of said inner reaction chamber.

6. The reactor according to claim 1, said shell being cylindrical.

7. The reactor according to claim 4, wherein said central duct communicates with the peripheral zone of the inner reaction chamber, said peripheral zone being delimited internally by the central duct and externally by said shell, and said peripheral zone communicating with said outer chamber.

8. The reactor according to claim 7, wherein said shell extends up to a height greater than the height of said central duct and a top edge of said shell acts as an overflow distributor for feeding said outer reaction chamber.

9. The reactor according to claim 4, comprising heating means which are housed inside said peripheral zone of the inner reaction chamber.

10. The reactor according to claim 1, said inner chamber being cylindrical and said outer chamber being an annular chamber around said inner chamber.

11. The reactor according to claim 1, comprising a distributor connected to said at least one gaseous ammonia inlet and configured to allow the introduction of ammonia in a distributed manner inside said outer chamber.

12. The reactor according to claim 11, said distributor comprising a toroidal body housed substantially at the base of the outer chamber.

13. The reactor according to claim 1, said header for the liquid melamine being housed at the bottom of said outer chamber.

14. The reactor according to claim 1, comprising also a scrubber section situated in the top part of the said reactor above said inner chamber and outer chamber, and arranged to collect the gases coming from said chambers.

15. A plant for converting urea into melamine using the high-pressure process, comprising at least one reactor according to claim 1.

16. A process for the high-pressure synthesis of melamine from urea, comprising:
  a primary conversion step inside a first chamber delimited by a shell inside a reactor body, resulting in crude melamine melt,
  a secondary step of stripping of said crude melamine melt inside a second reaction chamber, which is arranged coaxially around said first chamber, inside said reactor body,
  wherein said stripping is performed with gaseous ammonia, flowing upward in the second reaction chamber, and in counter-current with a descendant crude melamine melt,
  and melamine melt is withdrawn after stripping from said second reaction chamber.

17. The process according to claim 16, said secondary stripping being carried out with gaseous ammonia.

18. The process according to claim 16, also comprising the step of scrubbing of melamine off-gases produced during said primary and secondary steps, inside a scrubber section positioned above said coaxial reaction chambers and inside said reactor body.

19. The process according to claim 16, said pressure being higher than 70 bar.

20. The process according to claim 16, said pressure being between 70 and 250 bar.

* * * * *